(12) United States Patent
Lavielle et al.

(10) Patent No.: US 6,998,403 B2
(45) Date of Patent: Feb. 14, 2006

(54) BENZOINDOLINE COMPOUNDS

(75) Inventors: Gilbert Lavielle, La Celle Saint Cloud (FR); Olivier Muller, Pontoise (FR); Mark Millan, Le Pecq (FR); Alain Gobert, Rueil-Malmaison (FR); Benjamin Di Cara, Cassis (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 3 days.

(21) Appl. No.: 10/925,712

(22) Filed: Aug. 25, 2004

(65) Prior Publication Data

US 2005/0059675 A1    Mar. 17, 2005

(30) Foreign Application Priority Data

Sep. 16, 2003 (FR) .................................. 03 10828

(51) Int. Cl.
*A61K 31/496* (2006.01)
*C07D 403/12* (2006.01)
(52) U.S. Cl. .................................. 514/254.08; 544/372
(58) Field of Classification Search ................ 544/372; 514/254.08
See application file for complete search history.

(56) References Cited

U.S. PATENT DOCUMENTS

2002/0025965 A1 *  2/2002  Lavielle et al. ........ 514/254.05

FOREIGN PATENT DOCUMENTS

EP           1170288 A2 *  1/2002

OTHER PUBLICATIONS

Gaster et al. Annual Reports in Medicinal Chemistry, vol. 33, p. 21-30 (1998).*
Brefel-Courbon et al. Drug Therapy 10, pp. 189-207 (1998).*
Hoffman in Basic & Clinical Pharmacology (6th ed.) edited by Bertram G. Katzung, pp. 132-136 (1995).*
Invernizzi, et al., *Prog. Neuropsychophamacol. Bio. Psychiatry*, 2004, 28, 819-827.
Millan, et al., *J. Psychopharmacol.*, 2000, 14, 114-138.
Di Matteo, et al., *Trends Pharmacol. Sci.*, 2001, 22, 229-232.
Done, et al., *Neuropharmacology*, 1994, 33, 411-421.
O'Neill, et al., *Pharmacology, Biochemistry and Behavior*, 1999, 63, 237-243.
Reavill, et al., *British Journal of Psychopharmacology*, 1999, 126, 572-574.
Herrick-Davis, et al., *Journal of Pharmacology and Experimental Therapeutics*, 2000, 295, 226-232.
Wood, et al., *Drug Development Research*, 2001, 54, 88-94.
Paiva, et al., *Psychopharmacology*, 1988, 96, 395-399.
Dugovic, *Journal Sleep Research*, 1992, 1, 1163-1168.
Landolt, et al., *Neuropsychopharmacology*, 1999, 21, 455-466.
Sharpley, et al., *Biological Psychiatry*, 2000, 47, 468-470.
Foreman, et al., *Life Sciences*, 1989, 45, 1263-1270.
Klint, et al., *Psychopharmacology*, 1995, 119, 291-294.
Hirschfeld, *Journal of Clinical Psychiatry*, 60 Suppl. 17:32-35, 1999.
Popova, et al., *Neuroendocrinology*, 2002, 76, 28-34.
McMahon, et al., *Journal of Neuroscience*, 2001, 21, 7781-7787.
Filip, et al., *Pharmacology, Biochemistry and Behaviour*, 2002, 71, 545-756.
Fox, et al., *Drug News and Perspectives*, 1999, 12:477-483.
Fox, et al., *Movement Disorders*, 2000, 15:1064-1069.
Sara, et al., *Behavioural Neural Biology*, 1989, 51, 401-411.

(Continued)

*Primary Examiner*—Emily Bernhardt
(74) *Attorney, Agent, or Firm*—Hueschen and Sage

(57) ABSTRACT

A compound of formula (I):

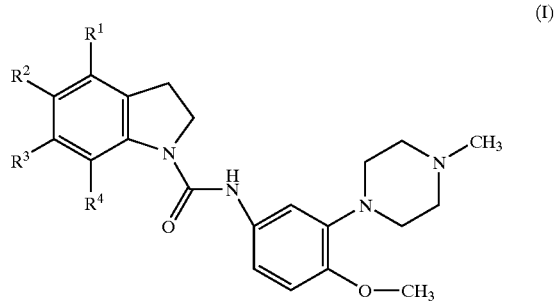

wherein:
$R^1$ and $R^2$ together form a benzo ring optionally substituted by halogen or by alkyl, alkoxy, cyano, nitro, hydroxy, amino, alkylamino, dialkylamino or trifluoromethyl, and $R^3$ and $R^4$ represent hydrogen, or $R^1$ and $R^4$ represent hydrogen and $R^2$ and $R^3$ together form a benzo ring optionally substituted by halogen or by alkyl, alkoxy, cyano, nitro, hydroxy, amino, alkylamino, dialkylamino or trifluoromethyl, or $R^1$ and $R^2$ represent hydrogen and $R^3$ and $R^4$ together form a benzo ring optionally substituted by halogen or by alkyl, alkoxy, cyano, nitro, hydroxy, amino, alkylamino, dialkylamino or trifluoromethyl, addition salts thereof with a pharmaceutically acceptable acid or base, and methods of treating conditions susceptible to $\alpha_2$-AR/5-$HT_{2C}$ antagonists.

5 Claims, No Drawings

OTHER PUBLICATIONS

Smith, et al., *Journal of Psychopharmacology*, 1992, 6, 376-381.
Coull, et al., *Psychopharmacology*, 1996, 123, 239-249.
Tellez, et al., *European Journal of Pharmacology*, 1995, 277, 113-116.
Haapalinna, et al., *European Journal of Pharmacology*, 1998, 347, 29-40.
"Dexefaroxan, efaroxan, L-0046, RX-821037", *Pharmaproject*, Phase II Clinical Trial (2005).
Nutt, *J. Psychopharmacology*, 1994, 8, 193-195.
Litman, et al., *British Journal of Psychiatry*, 1996, 168, 571-579.
Hertel, et al., *Science*, 1999, 286, 105-107.
"Idazoxan, CGP-25811A, L0022, RX-781094", *Pharmaproject*, Phase II Clinical Trial (2005).
"Fipamezol, JP-1730", *Pharmaproject*, Phase II Clinical Trial (2005).
Grondin, et al., *Naunyn Schmiedebergs Archives of Pharmacology*, 2000, Feb:361, 181-186.
Rascol, et al., *Mov. Disord.*, 2001, 16, 708-713.
Brown, et al., *Investigational Drugs*, 2002, 5, 454-468.
Clark, et al., *Neuroendocrinology*, 1985, 41, 36-43.
Reid, et al., *Lancet*, 1987, 22, (8556):421-423.
Koskinen, et al., *Physiology and Behaviour*, 1991, 50, 589-593.
Kunelius, et al., *Urology*, 1997, 49, 441-444.

\* cited by examiner

BENZOINDOLINE COMPOUNDS

The present invention relates to new benzoindoline compounds.

1. Field of the Invention

The compounds of the invention have a novel benzoindoline structure providing them with their double $\alpha_2$-AR/5-HT$_{2C}$ antagonist character and are therefore useful in the treatment of depression, anxiety, schizophrenia, Parkinson's disease, cognitive disorders, disorders of the libido and sexual dysfunctions, sleep disorders and impulsive behaviour disorders.

The present invention relates to new benzoindoline compounds, which constitute a selection with respect to the compounds described in application EP-1170288 to process for their preparation and to pharmaceutical composition. Those compounds are novel and differ from those described and mentioned as examples in application EP-1170288 not only in the absence of a halogen atom on the indoline but, especially, in the presence of a benzo group fused to the indoline group.

Surprisingly, the introduction of that group provides the compounds of the invention with pharmacological activities that are clearly superior to those of the structurally closest compound of the prior art (Example 11 of application EP-1170288: 6-chloro-5-fluoro-N-[4-methoxy-3-(4-methyl-1-piperazinyl)phenyl]-1-indoline-carboxamide).

Use of the benzoindoline radical has accordingly made possible a remarkable improvement in the pharmacological properties of the compounds of the invention.

2. Background of the Invention

The frontal cortex plays an essential part in the processes controlling the altered functions in psychiatric disorders. In particular, it is now recognised that disturbance of noradrenergic, dopaminergic and cholinergic transmission is strongly implicated in the aetiology of those various disorders. For example, in the case of depression, activity of those neuromediators is reduced in the corticolimbic regions.

Among the various classes of auto- and hetero-receptors of monoamines implicated in the mechanisms of regulation, $\alpha_2$-AR (adreno receptors) and 5-HT$_{2C}$ receptors have been found to be of major importance. Those two receptor subtypes act in the same direction by inhibiting dopaminergic and adrenergic transmission. On the one hand, inhibitory control is exerted by $\alpha_2$-AR receptors on dopaminergic, noradrenergic and cholinergic neurons [*The Journal of Pharmacology and Experimental Therapeutics*, 270, 958 (1994); *European Journal of Neuroscience*, 12, 1079–1095 (2000), *The Journal of Pharmacology and Experimental Therapeutics*, 305, 338–346 (2003)], and, on the other hand, 5-HT$_{2C}$ receptors exert inhibitory control on dopaminergic and noradrenergic transmission [*Neuropharmacology*, 36, 609 (1997)].

Compounds binding to one or other of those receptor classes have, in the past, demonstrated their potential for the treatment of a number of pathologies.

For example, the beneficial role of $\alpha_2$-AR antagonist compounds has been studied in the treatment of cognitive disorders [*Psychopharmacology*, 123, 239–249 (1996); *Journal of Psychopharmacology*, 6, 3, 376–381 (1992); *Neuroscience Letters*, 142, 36–40 (1992); *European Journal of Pharmacology*, 277, 113–116 (1995)], Parkinson's disease [*CNS Drugs*, 10, 189 (1998)], disorders of the libido and sexual dysfunctions [*Journal of Pharmacology*, 11, 72 (1997); *Urology*, 49, 3, 441–444 (1997); *International Journal of Impotence Research*, 12, S70–S74 (2000); *International Journal of Impotence Research*, 12, Suppl 1, S75–S80 (2000); *World Journal of Urology*, 19, 51–56 (2001)], schizophrenia [*British Journal of Pharmacology*, 124, 1550–1556 (1998)] and depression [*European Journal of Neuroscience*, 12, 1079–95 (2000); *The Journal of Pharmacology and Experimental Therapeutics*, 277 (2), 852–60 (1997); *Naulnyn-Schmiedeberg's Archiv. Pharmacol.*, 355 (1), 20–9 (1997)].

Likewise, 5-HT$_{2C}$ receptor antagonist compounds have demonstrated their usefulness in the treatment of sexual dysfunctions [*Life Sciences*, 45, 1263–1270 (1989); *Pharmacological Biochemistry and Behavior*, 39, 605–612 (1991); *Psychopharmacology*, 119, 291–294 (1995); *Neuroendocrinology*, 76, 28–34 (2002)] and Parkinson's disease [*Drug News Perspect*, 12 (8), 477–483 (1999)], as well as depression [*Prog. Neuro-Psychopharmaco Bio. Psychiat.*, 18, 563–574 (1994); *British Journal of Psychiatry*, 171, 444–448 (1997); *Neuropharmacology*, 39, 1222–1236 (2000)], anxiety [*British Journal of Pharmacology*, 117, 427 (1996)], schizophrenia [*Neuroscience Letter*, 181, 65 (1996); *The Journal of Pharmacology and Experimental Therapeutics*, 295, 1, 226–232 (2000); *Molecular Psychiatry*, 6, 373–379 (2001); *The Journal of Neuroscience*, 21, 19, 7781–7787 (2001); *Pharmacology, Biochemistry and Behavior*, 71, 745–756 (2002); *Psychopharmacology*, 162, 55–62 (2002)], impulsive behaviour disorders [*The Journal of Pharmacology and Experimental Therapeutics*, 298 (2), 581–591 (2001); *Brain research*, 835, 104–112 (1999)] and sleep disorders [*Psychopharmacology*, 96, 395–399 (1988); *Neuropsychopharmacology*, 21, 455–466 (1999); *Biological Psychiatry*, 47, 468–470 (2000); *Pharmacology, Biochemistry and Behavior*, 71, 599–605 (2002)].

Compounds having a double $\alpha_2$-AR and 5-HT$_{2C}$ antagonist character may be highly useful to clinicians in obtaining, by administration of a single compound, a considerably reinforced action, by an effect of synergy, in restoring neurotransmission. A compound of that kind, moreover, has a considerable advantage over the administration of two different compounds.

The compounds of the invention have a novel benzoindoline structure providing them with their double $\alpha_2$-AR/5-HT$_{2C}$ antagonist character and are therefore useful in the treatment of depression, anxiety, schizophrenia, Parkinson's disease, cognitive disorders, disorders of the libido and sexual dysfunctions, sleep disorders and impulsive behaviour disorders.

The present invention relates to new benzoindoline compounds which constitute a selection with respect to the compounds described in application EP-1170288. Those compounds are novel and differ from those described and mentioned as examples in application EP-1170288 not only in the absence of a halogen atom on the indoline but, especially, in the presence of a benzo group fused to the indoline group.

Surprisingly, the introduction of that group provides the compounds of the invention with pharmacological activities that are clearly superior to those of the structurally closest compound of the prior art (Example 11 of application EP-1170288: 6-chloro-5-fluoro-N-[ 4-methoxy-3-(4-methyl-1-piperazinyl)phenyl]-1-indoline-carboxamide).

Use of the benzoindoline radical has accordingly made possible a remarkable improvement in the pharmacological properties of the compounds of the invention.

DETAILED DESCRIPTION OF THE INVENTION

More specifically, the present invention relates to compounds of formula (I):

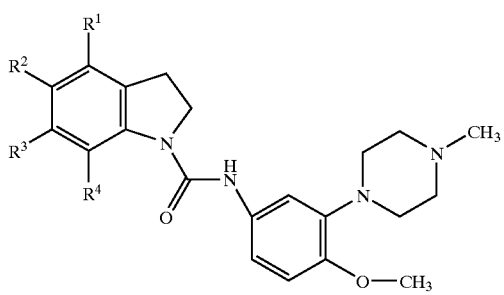

wherein:
R$^1$ and R$^2$ together form a benzo ring optionally substituted by a halogen atom or by an alkyl, alkoxy, cyano, nitro, hydroxy, amino, alkylamino, dialkylamino or trifluoromethyl group, and R$^3$ and R$^4$ represent a hydrogen atom,
or
R$^1$ and R$^4$ represent a hydrogen atom and R$^2$ and R$^3$ together form a benzo ring optionally substituted by a halogen atom or by an alkyl, alkoxy, cyano, nitro, hydroxy, amino, alkylamino, dialkylamino or trifluoromethyl group,
or
R$^1$ and R$^2$ represent a hydrogen atom and R$^3$ and R$^4$ together form a benzo ring optionally substituted by a halogen atom or by an alkyl, alkoxy, cyano, nitro, hydroxy, amino, alkylamino, dialkylamino or trifluoromethyl group, to their enantiomers and diastereoisomers, and to addition salts thereof with a pharmaceutically acceptable acid or base,
it being understood that:
the term "alkyl" denotes a linear or branched hydrocarbon chain containing from 1 to 6 carbon atoms,
the term "alkoxy" denotes a linear or branched alkyl-oxy group containing from 1 to 6 carbon atoms.

Among the pharmaceutically acceptable acids there may be mentioned hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid etc.

Among the pharmaceutically acceptable bases there may be mentioned sodium hydroxide, potassium hydroxide, triethylamine, tert-butylamine etc.

An advantageous aspect of the invention relates to compounds wherein R$^1$ and R$^2$ together form a benzo ring optionally substituted by a halogen atom or by an alkyl, alkoxy, cyano, nitro, hydroxy, amino, alkylamino, dialkylamino or trifluoromethyl group, and R$^3$ and R$^4$ represent a hydrogen atom.

Among the preferred compounds of the invention there may be mentioned, more especially, N-[4-methoxy-3-(4-methyl-1-piperazinyl)phenyl]-1,2-dihydro-3H-benzo[e]-indole-3-carboxamide.

The present invention relates also to a process for the preparation of compounds of formula (I), characterised in that there is used as starting material a benzoindole compound of formula (II):

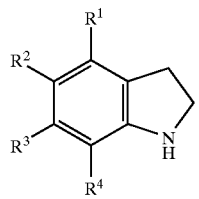

wherein R$^1$, R$^2$, R$^3$ and R$^4$ are as defined for formula (I), which is condensed with a compound of formula (III):

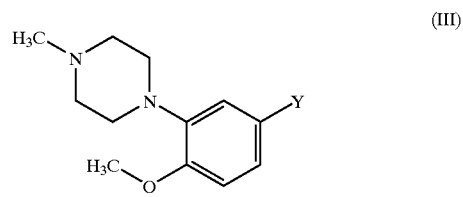

wherein Y represents a group —N=C=O or —C(O)—N$_3$, to yield the compound of formula (I),
which may be purified, if necessary, according to a conventional purification technique,
which is separated into its isomers (diastereoisomers and enantiomers), if necessary, by a conventional separation technique,
which is converted, if desired, into addition salts thereof with a pharmaceutically acceptable acid or base,
it being understood that the indoline of formula (II) is prepared according to known procedures, for example starting from the corresponding nitronaphthylacetonitrile compound.

The present invention relates also to pharmaceutical compositions comprising as active ingredient at least one compound of formula (I), alone or in combination with one or more inert, non-toxic, pharmaceutically acceptable excipients or carriers.

Among the pharmaceutical compositions according to the invention there may be mentioned more especially those that are suitable for oral, parenteral, nasal or transdermal administration, tablets or dragees, sublingual tablets, gelatin capsules, lozenges, suppositories, creams, ointments, dermal gels etc.

The useful dosage varies according to the age and weight of the patient, the nature and severity of the disorder, and also the administration route, which may be oral, nasal, rectal or parenteral. The unit dose generally ranges from 0.05 to 500 mg per 24 hours for treatment in 1 to 3 administrations.

The Examples which follow illustrate the invention without limiting it in any way.

The structures of the compounds described have been confirmed by conventional spectroscopic and spectrometric techniques.

The starting materials used are known products or are prepared according to known procedures.

PREPARATION 1

2,3-Dihydro-1H-benzo[e]indole

Step A: (2-Nitro-1-naphthyl)acetonitrile

Prepare a solution of 53.5 g (0.477 mol) of potassium tert.-butanolate in 400 ml of dimethylformamide. Cool the resulting solution to −10° C. and add thereto, over the course of about 1 hour, a solution of 40 g of 4-chlorophenoxyacetonitrile (0.24 mol) and 37 g of 2-nitronaphthalene (0.213 mol) in 200 ml of dimethylformamide. After 2 hours at −5° C., pour the mixture into 4 litres of water containing 1 litre of concentrated hydrochloric acid and extract the aqueous phase with 3×500 ml of dichloromethane. Wash the organic phase with 300 ml of water, dry it over magnesium sulphate, filter and then evaporate off the solvent.

65 g of product are obtained.

Recrystallise that 65 g from a mixture of cyclohexane/ethyl acetate:50/50:v/v.

Step B: 3H-Benzo[e]indole

At ambient temperature and under 4 bars of hydrogen, hydrogenate 33 g of (2-nitro-1-naphthyl)acetonitrile (0.155 mol) dissolved in 630 ml of ethanol containing 10% water and 6.3 ml of pure acetic acid, using 19 g of 10% palladium-on-carbon. After absorption has ceased, filter off the catalyst, concentrate the solvent in vacuo and then take up the residue in 250 ml of dichloromethane; wash the organic phase with 100 ml of 0.1N potassium hydroxide solution and then dry the organic phase over magnesium sulphate, filter and concentrate.

The residue is purified by chromatography over silica, the eluant being cyclohexane/ethyl acetate:80/20:v/v.

Step C: 2.3-Dihydro-1H-benzo[e]indole

10 g (0.06 mol) of the compound prepared in the previous step are dissolved in 50 ml of tetrahydrofuran. To the resulting solution, at 0° C., add 120 ml of borane/THF complex as a 1M solution in tetrahydrofuran, and then 120 ml of trifluoroacetic acid. After 30 minutes, add, at 0° C., 6 ml of water, stir for 15 minutes and then concentrate the mixture to dryness. The residue is taken up in 200 ml of dichloromethane and washed with 200 ml of 1N sodium hydroxide solution. The organic phase is dried over magnesium sulphate, filtered and concentrated.

PREPARATION 2

2,3-Dihydro-1H-benzo[f]indole

The experiment protocol for reducing 1H-benzo[f]indole is the same as that of Preparation 1, Step C. Synthesis of the starting material 1H-benzo[f]indole has been described in the literature [*Tetrahedron*, 49, 33, 7353 (1993); *Heterocycles*, 24, 7, 1845, (1986)].

PREPARATION 3

2,3-Dihydro-1H-benzole[e]indole-6-carbonitrile

Step A: N-(5-Cyano-2-naphthyl)acetamide

To 25 g of N-(5,6,7,8-tetrahydronaphth-2-yl)acetamide cooled to 0° C. add, successively, 70 ml of pure trimethylsilyl cyanide and then 30 g of dichlorodicyanoquinone in 70 ml of dichloromethane. After 3 hours at ambient temperature, again add a solution of 60 g of dichlorodicyanoquinone in 140 ml of dichloromethane. Stir at 20° C. for 12 hours and then heat at 60° C. for 8 hours.

After neutralising with saturated sodium hydrogen carbonate solution, the organic phase is separated off and washed with water. The residue obtained after concentration is purified by chromatography over silica gel using a mixture of cyclohexane/ethyl acetate:80/20:v/v as eluant.

Step B: N-(1-Bromo-5-cyano-2-naphthyl)acetamide

To a solution, cooled to −5° C., of 50 g (0.238 mol) of the product synthesised in the previous step in 500 ml of dichloromethane and 25 ml of pyridine, add 39.8 g of bromine dissolved in 200 ml of dichloromethane. Then stir vigorously for 4 hours at ambient temperature; subsequently dilute with 500 ml of dichloromethane, wash the organic phase twice with 300 ml of water, dry and concentrate. The residue is recrystallised from a mixture of dichloromethane/methanol:50/50:v/v.

Step C: 6-Amino-5-bromo-1-naphthonitrile

Heat at 80° C., for 6 hours, a mixture of 12.5 g (0.043 mol) of the product synthesised in the previous step, 3.6 g of sodium hydroxide, 195 ml of methanol and 65 ml of water. After evaporating off the methanol, the aqueous phase is extracted twice with dichloromethane. The latter is subsequently dried and evaporated off. The residue is crystallised from a dichloromethane/methanol mixture.

Step D: Ethyl 1-bromo-5-cyano-2-naphthylcarbamate

Add, at 0° C., 19 ml of ethyl chloroformate to a solution of 33 g (0.133 mol) of the product synthesised in the previous step in 200 ml of pyridine. After 1 hour at 5° C., evaporate off the solvent, take up the residue in 500 ml of dichloromethane, wash the organic phase 3 times with 100 ml of 0.1N hydrochloric acid and then with 200 ml of 10% sodium hydrogen carbonate solution and finally once with water. The residue obtained by evaporation is recrystallised from a dichloromethane/methanol mixture.

Step E: Ethyl 5-cyano-1-[(trimethylsilyl)ethynyl]-2-naphthylcarbamate

In a steel reactor, mix 14.1 g (0.044 mol) of the product synthesised in the previous step, 11 ml of trimethylsilylacetylene, 13 ml of triethylamine, 670 mg of cuprous iodide and 1.54 g of dichloro-bis(triphenylphosphine)palladium. Then close the reactor and heat the reaction mixture at 80° C. for 4 hours. Dilute with 200 ml of dichloromethane and 100 ml of water, filter the mixture, separate off the organic phase, dry it and evaporate off the solvent in vacuo. The residue obtained is purified by chromatography over silica gel, using a mixture of cyclohexane/ethyl acetate:90/10:v/v as eluant, followed by crystallisation from the same solvent.

Step F: 3H-Benzo[e]indole-6-carbonitrile

To a solution of 2.74 g of sodium in 280 ml of dry ethanol add 10 g (0.0297 mol) of the product synthesised in the previous step and heat the mixture at reflux for one hour. After evaporating off the solvent, the residue is taken up in 200 ml of dichloromethane and the organic phase is washed with 200 ml of water. After evaporation, the residue is purified by chromatography over silica gel using a mixture of cyclohexane/ethyl acetate:80/20:v/v as eluant.

Step G: 2.3-Dihydro-1H-benzo[e]indole-6-carbonitrile

The experiment protocol for reducing 3H-benzo[e]indole-6-carbonitrile is the same as that of Preparation 1, Step C.

PREPARATION 4

7-Methoxy-2,3-dihydro-1H-benzo[e]indole

Step A: 6-Methoxy-3,4-dihydro-1(2H)-naphthalenone Oxime

Dissolve 100 g (0.57 mol) of 6-methoxy-1-tetralone in 2.5 litres of a mixture of ethanol/water: 80/20. There are then added, at ambient temperature, 85 g (1.04 mol) of sodium acetate and 43 g (0.62 mol) of hydroxylamine hydrochloride. Heat the suspension at reflux for 4 hours. Dilute the mixture with 5 litres of water and extract with ethyl ether, wash with water, dry over magnesium sulphate and filter. After evaporating off the solvent, 99 g of a beige solid are obtained.

Step B: 2-Amino-6-methoxy-3,4-dihydro-1(2H)-naphthalenone

Dissolve 50 g (0.26 mol) of the product synthesised in the previous step in 185 ml of pyridine and then add, at ambient temperature, 54.9 g (0.29 mol) of para-toluenesulphonyl chloride. After 24 hours, pour onto ice and then filter off the precipitate. Take up the precipitate in dichloromethane and wash with water; dry the organic phase over magnesium sulphate and filter. After evaporating off the solvent, 89 g of a yellow solid (intermediate product 1) are obtained.

Add 7.48 g (0.32 mol) of sodium to a mixture of toluene/ethanol: 720/148 ml. After dissolution, dilute with 940 ml of toluene and rapidly add 117 g (0.34 mol) of intermediate product 1. After 24 hours at ambient temperature, filter off the sodium para-toluenesulphonate, rinse with toluene, and then pour the organic solution into 10% hydrochloric acid solution (1.1 litres). Separate off, extract once with water and then evaporate the aqueous phase. Take up the residue in ethanol and then filter off the precipitate. 46.5 g of a beige solid in the form of the hydrochloride are obtained.

Step C: N-Ethyl-N'-(6-methoxy-1-oxo-1,2,3,4-tetrahydro-2-naphthyl)urea

Pour 4.77 g (0.044 mol) of ethyl chloroformate at 0° C. into 5 g (0.022 mol) of 2-amino-6-met dissolved in pyridine. After two hours at ambient temperature, concentrate the pyridine, take up in dichloromethane and then wash the organic phase with 0.1N hydrochloric acid solution and then with saturated sodium hydrogen carbonate solution and water; dry over magnesium sulphate, filter, and evaporate off the solvent. 5.48 g of an orange solid are obtained.

Step D: N-Ethyl-N'-(6-methoxy-1,2,3,4-tetrahydro-2-naphthyl)urea

At 60° C. and under atmospheric pressure, hydrogenate 98 g (0.37 mol) of the product previously prepared in Step C and dissolved in 1.5 litres of ethanol, using 10 g of 5% palladium-on-carbon. After the absorption has ceased, filter off the catalyst and concentrate the solvent in vacuo. 88.2 g of an oil are obtained.

Step E: N-Ethyl-N'-(6-methoxy-2-naphthyl)urea

Dissolve 7.42 g (0.0298 mol) of the product synthesised in the previous step in 100 ml of toluene. Add 13.51 g (0.0595 mol) of dichlorodicyanoquinone and heat at reflux for 30 minutes. Filter off the precipitate at ambient temperature, rinse with toluene and then evaporate off the solvent. The residue is purified by chromatography over silica gel using pure dichloromethane as eluant. 4 g of a grey solid are obtained.

Step F: 6-Methoxy-2-naphthylamine

Dissolve 3.5 g of the product synthesised in the previous step in 65 ml of ethanol and then add a solution of potassium hydroxide in 65 ml of water. After refluxing for 4 hours, filter off, at ambient temperature, the precipitate that is formed. Take up the crude product in dichloromethane and wash with water until neutral; dry over magnesium sulphate, filter off the precipitate and then evaporate off the solvent. 2.02 g of an orange solid are obtained.

Step G: 1-Iodo-6-methoxy-2-naphthylamine 28.2 g (0.16 mol) of the product synthesised in the previous step are dissolved in a mixture of dichloromethane/methanol: 1500/620 ml. To the resulting solution add, at ambient temperature, 56.7 g (0.16 mol) of benzyltrimethylammonium dichloroiodate and 21.2 g (0.212 mol) of calcium carbonate. After 30 minutes, filter off the insoluble material, then take up the organic phase with 10% sodium bisulphite solution and extract with ethyl ether. Dry over magnesium sulphate, filter and then evaporate. The residue is purified by chromatography over silica gel using a mixture of cyclohexane/ethyl acetate:70/30:v/v as eluant.

Step H: Ethyl 1-iodo-6-methoxy-2-naphthylcarbamate

Conversion of 1-iodo-6-methoxy-2-naphthylamine is carried out by applying the method described in Step C.

Step I: Ethyl 6-methoxy-1-[(trimethylsilyl)ethynyl]-2-naphthylcarbamate

Conversion of ethyl 1-iodo-6-methoxy-2-naphthylcarbamate is carried out by applying the method described in Preparation 3, Step E.

Step J: 7-Methoxy-3H-benzo[e]indole

Conversion of the compound of the previous step is carried out by applying the method described in Preparation 3, Step F.

Step K: 7-Methoxy-2,3-dihydro-1H-benzo[e]indole

The experiment protocol for reducing 7-methoxy-3H-benzo[e]indole is the same as that of Preparation 1, Step C.

PREPARATION 5

4-Methoxy-3-(4-methyl-1-piperazinyl)benzoyl Azide

At ambient temperature, add a solution of 5.3 g (0.025 mol) of phenyl dichlorophosphate in 100 ml of dichloromethane to a solution of 5 g (0.02 mol) of 4-methoxy-3-(4-methyl piperazin-1-yl)benzoic acid [*J. Med. Chem.*, 37 (15), 2255 (1994)] and 3.25 g (0.05 mol) of sodium azide in 4.05 ml of pyridine. After stirring for 12 hours, wash the organic phase with 100 ml of water, separate off the organic phase, dry it over magnesium sulphate and evaporate off the solvent in vacuo at 30° C.

EXAMPLE 1

N-[4-Methoxy-3-(4-methyl-1-piperazinyl)phenyl]-1,2-dihydro-3H-benzo[e]indole-3-carboxamide Hydrochloride Heat at reflux a solution of 29 g (0.105 mol) of the compound synthesised in Preparation 5 in 400 ml of toluene, then cool to 20° C. and add 100 ml of dichloromethane and then a solution of 18 g (0.105 mol) of the product obtained in Preparation 1. After stirring for 24 hours at 20° C., evaporate off the solvent and purify the residue by chromatography over silica using a mixture of dichloromethane/methanol/ammonia:95/5/0.5:v/v/v as eluant. The base is then converted into the salt by means of hydrochloric acid in ethanolic solution.

Melting point: 176–178° C.

EXAMPLE 2

N-[4-Methoxy-3-(4-methyl-1-piperazinyl)phenyl]-2,3-dihydro-1H-benzo[f]indole-1-carboxamide Hydrochloride The experiment protocol is the same as that of Example 1, starting from the product of Preparation 2.

EXAMPLE 3

6-Cyano-N-[4-methoxy-3-(4-methyl-1-piperazinyl)-phenyl]-1,2-dihydro-3H-benzo[e]-indole-3-carboxamide Hydrochloride The experiment protocol is the same as that of Example 1, starting from the product of Preparation 3.

EXAMPLE 4

7-Methoxy-N-[4-methoxy-3-(4-methyl-1-piperazinyl)-phenyl]-1,2-dihydro-3H-benzo[e]-indole-3-carboxamide Hydrochloride The experiment protocol is the same as that of Example 1, starting from the product of Preparation 4.

PHARMACOLOGICAL STUDIES

EXAMPLE A

Determination of the Affinity for $\alpha_2$-adrenergic Receptors in the Rat

The affinity was determined by competition experiments with [$^3$H]-RX 821,002. The membranes are prepared from the cerebral cortex of the rat and are incubated in triplicate with 0.4 nM [$^3$H]-RX 821,002 and the compound being tested in a final volume of 1.0 ml, for 60 minutes at 22° C. The incubation buffer contains 50 nM TRIS-HCl (pH 7.5), 1 mM EDTA and 100 $\mu$M GppNHp. The non-specific binding is determined using 10 $\mu$M phentolamine.

Data analysis: At the end of the incubation, the incubation medium is filtered through WHATMAN GF/B filters impregnated with 0.1% of polyethylenimine and washed three times with 5 ml of cooled buffer. The radioactivity retained on the filters is determined by liquid scintillation counting. The binding isotherms are analysed by non-linear regression.

Results: The compounds of the invention exhibit a specific $\alpha_2$-adrenergic receptor antagonist activity with, for example for the compound of Example 1, a pKi of 7.4, whereas for the comparative product (Example 11 of application EP-1 170288), 6-chloro-5-fluoro-N-[4-methoxy-3-(4-methyl-1-piperazinyl)phenyl]-1-indolinecarboxamide, the pKi is 6.4.

EXAMPLE B

Determination of the Affinity for 5-HT$_{2C}$ Receptors

The affinity of the compounds of the invention ws determined by competition experiments in the presence of [$^3$H]-mesulergine, in an incubation buffer Hepes 20 mM, EDTA 2 mM, ascorbic acid 0.1% (pH=7.7), at 22° C. The dissociation constant K$_D$ of [$^3$H]-mesulergine is 0.54 mM. The non-specific fraction is defined in the presence of 1 $\mu$M mianserin, the latter also being the reference product for each experiment.

At the end of the incubation period, the medium is filtered through GF/B-Unifilter filters pre-treated with PEI (0.1%), followed by washing three times with the incubation buffer. The radioactivity retained on the filters is determined by liquid scintillation counting. The binding isotherms are analysed by non-linear regression in order to determine the IC$_{50}$ values. They are converted into pK$_i$ (where K$_i$ is the dissociation constant).

It appears that the compounds of the invention have a high affinity for 5-HT$_{2C}$ receptors; for example, the compound of Example 1 has a pKi of 8.2 whereas the comparative compound (Example 11 of application EP-1170288), 6-chloro-5-fluoro-N-[4-methoxy-3-(4-methyl-1-piperazinyl)phenyl]-1-indolinecarboxamide, has a pKi of 7.4.

EXAMPLE C

Measurement of Neurotransmitters in the Frontal Cortex of Rats

Dialysis.

The surgery is performed under pentobarbital-induced anaesthesia (60 mg/kg, i.p.). Male Wistar rats, 200–220 g (Iffa Credo, Arbresle, France), are placed in a Kopf stereotaxic device and a cannula guide (CMAMicrodialyse AB, Stockholm, Sweden) is implanted in the frontal cortex at the coordinates (in mm): anteroposterior: +2.2, lateral: ±0.6, ventral deviation: −0.2. The rats are placed in separate cages and recover from the anaesthesia over 5 days. On the day of the dialysis, a Cuprophan CMA/11 probe (length: 4 mm; ext. dia.: 0.24 mm) is introduced into the guide and perfused at 1 $\mu$l/min. with a solution of NaCl: 147.2 mM; KCl: 4 mM; CaCl$_2$: 2.3 mM adjusted to pH 7.3 with a phosphate buffer. Two hours after implantation, samples of dialysate are collected every 20 minutes for 4 hours. Three baseline samples are collected before administration of the drug.

Chromatography.

Noradrenaline (NA) and dopamine (DA) are measured as follows: 20 $\mu$l of dialysate sample are diluted with 20 $\mu$l of mobile phase (NaH$_2$PO$_4$: 75 mM, EDTA: 20 $\mu$M, sodium decanesulphonate: 1 mM, methanol: 17.5%, triethylamine: 0.01%, pH: 5.70) and 33 $\mu$l are analysed by HPLC using, for separation, an inverse-phase column (Hypersil C 18, 150×4.6 mm; particle size 5 $\mu$m) thermostatically controlled at 43° C. and, for quantification, a coulometric detector (ESA5014, Coulochem II, ESA, Chelmsford, USA). The potential of the first electrode is −90 mV (reduction) and that of the second +280 mV (oxidation). The mobile phase flow rate is 2 ml/min. The sensitivity limit for NA and DA is 0.2 pg.

Acetylcholine (ACh) is measured and quantified in the absence of acetylcholine esterase (AChE) inhibitor 20 $\mu$l of dialysate sample are collected in 10 μl of 0.01% acetic acid. 20 μl aliquots are analysed by HPLC. The mobile phase is composed of $Na_2HPO_4$: 50 mM and ProClin: 0.5% (BAS, Congleton, UK), pH 8.2. The stationary phase is composed of a cation-exchange column (Sepstik, 530×1.0 mm, particle size 10 μm, BAS), a pre-column (choline oxidase/catalase enzymatic reactor, 55×1 mm, BAS) and a post-column (choline oxidase/AChE enzymatic reactor, 50×1 mm, BAS). The system is maintained at 35° C. Quantification is carried out by means of an amperometric detector (LC-4B, BAS). A layer of peroxidase-redox polymer is deposited on the vitreous carbon working electrode (MF2098, BAS). The potential of that electrode is +100 mV relative to the Ag/AgCl reference electrode. The mobile phase flow rate is 0.14 ml/min. The sensitivity limit for ACh is 0.1 pg.

By way of example, the compound of Example 1 (10.0 mg/kg, s.c.) causes a substantial increase in the extracellular concentrations of NA, DA and ACh in the dialysates collected from the frontal cortex of conscious rats (Table 1). The comparative compound (Example 11 of application EP-1170288), 6-chloro-5-fluoro-N-[4-methoxy-3-(4-methyl-1-piperazinyl)phenyl]-1-indolinecarboxamide, (10.0 mg/kg, s.c.), causes a very modest increase in the extracellular concentrations of NA and DA and no change in the extracellular concentration of ACh (Table 1). The levels of NA, DA and ACh are expressed as the percentage area beneath the curve (% AbC) ±S.E.M. of times 20 min. to 120 min. after administration of the drug. The effects of the compound of Example 1 are compared (ANOVA) with those obtained in animals treated with the solvent or with 6-chloro-5-fluoro-N-[4-methoxy-3-(4-methyl-1-piperazinyl)phenyl]-1-indoline-carboxamide.

TABLE 1

| %AbC ± S.E.M. | Solvent | Compound of Example 1 | Comparative compound (Example 11–EP-1170288) |
|---|---|---|---|
| NA | +18.2 ± 5.0 | +105.4 ± 7.3[a,b] | +39.8 ± 6.7 |
| DA | +4.4 ± 2.5 | +52.9 ± 6.6[a] | +19.5 ± 4.9 |
| ACh | +16.5 ± 5.5 | +107.7 ± 13.5[a,b] | +15.1 ± 12.3 |

[a] $P < 0.005$ versus solvent and
[b] $P < 0.05$ versus 6-chloro-5-fluoro-N-[4-methoxy-3-(4-methyl-1-piperazinyl)phenyl]-1-indolinecarboxamide.

EXAMPLE D

Pharmaceutical Composition

Formula for the Preparation of 1000 Tablets Each Comprising 10 mg of Active Ingredient

| | |
|---|---|
| compound of Example 1 | 10 g |
| hydroxypropylcellulose | 2 g |
| wheat starch | 10 g |
| lactose | 100 g |
| magnesium stearate | 3 g |
| talc | 3 g |

The invention claimed is:

1. A compound selected from those of formula (I):

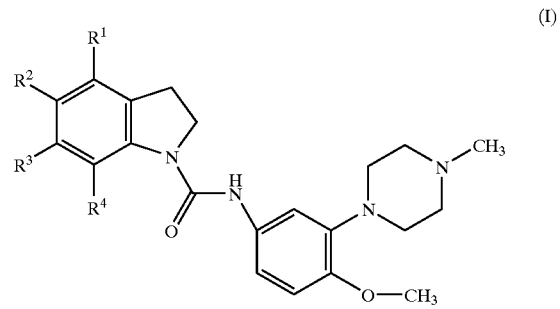

wherein:
$R^1$ and $R^2$ together form a benzo ring optionally substituted by halogen or by alkyl, alkoxy, cyano, nitro, hydroxy, amino, alkylamino, dialkylamino or trifluoromethyl, and $R^3$ and $R^4$ represent hydrogen,
or
$R^1$ and $R^4$ represent hydrogen and $R^2$ and $R^3$ together form a benzo ring optionally substituted by halogen or by alkyl, alkoxy, cyano, nitro, hydroxy, amino, alkylamino, dialkylamino or trifluoromethyl,
or
$R^1$ and $R^2$ represent hydrogen and $R^3$ and $R^4$ together form a benzo ring optionally substituted by halogen or by alkyl, alkoxy, cyano, nitro, hydroxy, amino, alkylamino, dialkylamino or trifluoromethyl,
its enantiomers, diastereoisomers, and addition salts thereof with a pharmaceutically acceptable acid or base,
it being understood that:
the term "alkyl" denotes a linear or branched hydrocarbon chain having from 1 to 6 carbon atoms,
the term "alkoxy" denotes a linear or branched alkyloxy group having from 1 to 6 carbon atoms.

2. A compound of claim 1, wherein $R^1$ and $R^2$ together form a benzo ring optionally substituted by halogen or by alkyl, alkoxy, cyano, nitro, hydroxy, amino, alkylamino, dialkylamino or trifluoromethyl, and $R^3$ and $R^4$ represent hydrogen, its enantiomers and diastereoisomers, and addition salts thereof with a pharmaceutically acceptable acid or base.

3. A compound of claim 1 which is N-[4-methoxy-3-(4-methyl-1-piperazinyl)phenyl]-1,2-dihydro-3H-benzo[e]indole-3-carboxamide, and its addition salts thereof with a pharmaceutically acceptable acid or base.

4. A pharmaceutical composition comprising as active principle an effective amount of a compound of claim 1, together with one or more pharmaceutically acceptable carriers, excipients or vehicles.

5. A method for treating an animal or human living body afflicted with a condition selected from depression, anxiety, impulsive behavior disorders, schizophrenia, and Parkinson's disease, comprising the step of administering to the living body an amount of a compound of claim 1 which is effective for alleviation of the condition.

* * * * *